US012092263B1

(12) United States Patent
Zhao et al.

(10) Patent No.: US 12,092,263 B1
(45) Date of Patent: Sep. 17, 2024

(54) DOUBLE-LAYER OIL FILM LUBRICATION ANALYSIS METHOD AND SYSTEM BASED ON FLOATING BUSHING

(71) Applicant: Harbin Engineering University, Heilongjiang (CN)

(72) Inventors: Bin Zhao, Heilongjiang (CN); Huaiqian Guo, Heilongjiang (CN); Wanyou Li, Heilongjiang (CN); Xiqun Lu, Heilongjiang (CN); Xuan Ma, Heilongjiang (CN); Xiujiang Shi, Heilongjiang (CN); Zhijun Shuai, Heilongjiang (CN); Yibin Guo, Heilongjiang (CN); Donghua Wang, Heilongjiang (CN); Hanzhang Xu, Heilongjiang (CN); Hongliang Li, Heilongjiang (CN); Lieyi Dong, Heilongjiang (CN)

(73) Assignee: Harbin Engineering University, Harbin (CN)

( * ) Notice: Subject to any disclaimer, the term of this patent is extended or adjusted under 35 U.S.C. 154(b) by 0 days.

(21) Appl. No.: 18/410,596

(22) Filed: Jan. 11, 2024

(30) Foreign Application Priority Data

Apr. 14, 2023 (CN) .......................... 202310404676.6

(51) Int. Cl.
*F16N 29/00* (2006.01)
*G01N 33/28* (2006.01)
*G01N 33/30* (2006.01)

(52) U.S. Cl.
CPC ......... *F16N 29/00* (2013.01); *G01N 33/2888* (2013.01); *G01N 33/30* (2013.01); *F16N 2250/00* (2013.01)

(58) Field of Classification Search
CPC .... G01N 33/30; G01N 33/2888; F16N 29/00; F16N 29/02; F16N 29/04; F16N 2250/00
See application file for complete search history.

(56) References Cited

U.S. PATENT DOCUMENTS 4,944,609 A * 7/1990 Salter, Jr. ................ F16C 13/02
384/118

FOREIGN PATENT DOCUMENTS

| CN | 113686231 A | 11/2021 | |
|---|---|---|---|
| CN | 114611433 A | 6/2022 | |
| WO | WO-2022162596 A1 * | 8/2022 | ........... B21B 31/074 |

* cited by examiner

*Primary Examiner* — Paul M. West

(57) ABSTRACT

Disclosed is a double-layer oil film lubrication analysis method and system based on a floating bushing. The method includes: determining a roller motion track and a floating bushing motion track according to a roller displacement and a floating bushing displacement; determining, when the motion tracks are closed end to end, minimum values of inner-layer and outer-layer oil film thickness of the floating bushing according to an oil film thickness at each moment; and determining that an abnormality exists in double-layer oil film lubrication when either of the minimum values of the inner-layer and outer-layer oil film thickness of the floating bushing is less than a preset oil film thickness threshold value. According to the present disclosure, more accurate abnormality analysis of double-layer oil film lubrication can be realized.

12 Claims, 4 Drawing Sheets

```
┌─────────────────────────────────────────────────────────────────┐
│ Determine an inner-layer oil film thickness and an outer-layer │ 101
│ oil film thickness of a floating bushing at each moment and     │
│ determine a roller displacement and a floating bushing          │
│ displacement at each moment during the rotation of a cam        │
└─────────────────────────────────────────────────────────────────┘
                              │
                              ▼
┌─────────────────────────────────────────────────────────────────┐
│ Determine a roller motion track and a floating bushing motion   │ 102
│ track according to the roller displacement and the floating     │
│ bushing displacement at each moment, respectively               │
└─────────────────────────────────────────────────────────────────┘
                              │
                              ▼
┌─────────────────────────────────────────────────────────────────┐
│ Determine, when the roller motion track and the floating        │ 103
│ bushing motion track are closed end to end, a minimum value of  │
│ the inner-layer oil film thickness and a minimum value of the   │
│ outer-layer oil film thickness of the floating bushing          │
│ according to the inner-layer oil film thickness and the outer-  │
│ layer oil film thickness of the floating bushing at each        │
│ moment, respectively                                            │
└─────────────────────────────────────────────────────────────────┘
                              │
                              ▼
┌─────────────────────────────────────────────────────────────────┐
│ Determine that an abnormality exists in double-layer oil film   │ 104
│ lubrication when either of the minimum value of the inner-layer │
│ oil film thickness and the minimum value of the outer-layer oil │
│ film thickness of the floating bushing is less than a preset    │
│ oil film thickness threshold value                              │
└─────────────────────────────────────────────────────────────────┘
```

FIG. 1

DOUBLE-LAYER OIL FILM LUBRICATION ANALYSIS METHOD AND SYSTEM BASED ON FLOATING BUSHING

CROSS-REFERENCE TO RELATED APPLICATIONS

This application claims priority of Chinese Patent Application No. 202310404676.6, filed on Apr. 14, 2023, the entire contents of which are incorporated herein by reference.

TECHNICAL FIELD

The present disclosure relates to the technical field of diesel engines, in particular to a double-layer oil film lubrication analysis method and system based on a floating bushing.

BACKGROUND

A combination structure of roller-floating bushing-roller pin is the key part of an oil supply mechanism of a diesel engine, and the lubricating performance of the structure will directly affect the reliability and life of the diesel engine. In the working process, the cam drives the roller to rotate, the roller pin is a fixed part, while the bushing is floating. A double-layer bearing oil film can be formed inside and outside the floating bushing, with a strong bearing capacity. At the same time, the floating bushing has a certain rotating speed, which can reduce a relative speed between the roller and the roller pin, thereby reducing friction power consumption and heat generation. Therefore, compared with a structure of roller-roller pin with single-layer oil film lubrication, the structure of roller-floating bushing-roller pin has the advantages of high bearing capacity and low friction temperature rise under the typical low-speed and heavy-load conditions of the oil supply mechanism of the traditional diesel engine. However, in actual work, the floating bushing often has abnormal locking, wear and other lubrication failures, affecting the reliability of the oil supply mechanism. However, the lubrication state of the roller-floating bush-roller pin of the oil supply mechanism when being identified is always in a stable working condition, so it is necessary to establish a more perfect transient lubrication model of the roller-floating bush-roller pin, which couples the kinematic and dynamic relationship of cam-roller with the transient lubrication of the roller-floating bushing-roller pin, and based on this, a more accurate double-layer oil film lubrication analysis of the roller-floating bushing-roller pin is realized.

SUMMARY

In view of the problems existing in the prior art, the present disclosure provides a double-layer oil film lubrication analysis method and system based on a floating bushing, which can more accurately analyze and determine the double-layer oil film lubrication state of the floating bushing.

In a first aspect, the present disclosure provides a double-layer oil film lubrication analysis method based on a floating bushing, including:
determining an inner-layer oil film thickness and an outer-layer oil film thickness of a floating bushing at each moment and determining a roller displacement and a floating bushing displacement at each moment during the rotation of a cam,
determining a roller motion track and a floating bushing motion track according to the roller displacement and the floating bushing displacement at each moment, respectively,
determining, when the roller motion track and the floating bushing motion track are closed end to end, a minimum value of the inner-layer oil film thickness and a minimum value of the outer-layer oil film thickness of the floating bushing according to the inner-layer oil film thickness and the outer-layer oil film thickness of the floating bushing at each moment, respectively, and
determining that an abnormality exists in double-layer oil film lubrication when either of the minimum value of the inner-layer oil film thickness and the minimum value of the outer-layer oil film thickness of the floating bushing is less than a preset oil film thickness threshold value.

Alternatively, structural parameters of a first combination structure are acquired, the first combination structure including a cam and a roller;
a time-varying rotating speed of the roller is calculated according to the structural parameters of the first combination structure;
the structural parameters of the second combination structure are acquired, the second combination structure including the roller, the floating bushing and the roller pin;
the inner-layer oil film thickness and the outer-layer oil film thickness of the floating bushing at the current moment are calculated according to the structural parameters of the second combination structure;
Reynolds-averaged Navier-Stokes (RANS) equations of the inner-layer and outer-layer oil films are solved according to the time-varying rotating speed of the roller, the inner-layer oil film thickness and the outer-layer oil film thickness, and an inner-layer oil film pressure and an outer-layer oil film pressure of the floating bushing at the current moment are obtained when a pressure converges;
an inner-layer elastic deformation and an outer-layer elastic deformation of the floating bushing are determined according to the inner-layer oil film pressure and the outer-layer oil film pressure, respectively;
the inner-layer elastic deformation and the outer-layer elastic deformation are substituted into an oil film thickness equation, and the inner-layer oil film pressure and the outer-layer oil film pressure of the floating bushing at the current moment are output when the elastic deformations converge and the inner and outer layers of the floating bushing reach a thermal equilibrium condition;
a roller displacement and a floating bushing displacement at the current moment are determined;
the roller motion track and the floating bushing motion track at the current moment are determined according to the roller displacement and the floating bushing displacement;
the structural parameters of the second combination structure at the next moment are acquired if either of the roller motion track and the floating bushing motion track is not closed end to end; and
the inner-layer oil film thickness and the outer-layer oil film thickness of the floating bushing at the next moment are determined according to the structural parameters of the second combination structure at the next moment.

Alternatively, the calculating a time-varying rotating speed of the roller according to the structural parameters of the first combination structure specifically includes:

calculating a pressure angle and radius of curvature of the cam according to cam profile parameters;

calculating a cam surface speed according to the pressure angle and radius of curvature of the cam;

calculating a roller surface speed according to the cam surface speed; and calculating the time-varying rotating speed of the roller according to the roller surface speed.

Alternatively, the determining a roller displacement and a floating bushing displacement at each moment specifically includes:

acquiring structural parameters of a first combination structure, the first combination structure including a cam and a roller;

calculating a time-varying load of the roller according to the structural parameters of the first combination structure; and determining a roller displacement and a floating bushing displacement at each moment according to the time-varying load of the roller, a kinematic equation between the roller and the floating bushing and a rotating speed equation of the floating bushing.

Alternatively, the time-varying load of the roller includes a spring-to-roller acting force, an inertial force, and a plunger oil chamber hydraulic pressure.

Alternatively, the preset oil film thickness threshold value is any value in a range of 0.8 microns to 1.2 microns.

In a second aspect, the present disclosure provides a double-layer oil film lubrication analysis system based on a floating bushing, including:

a first parameter determination module, configured to determine an inner-layer oil film thickness and an outer-layer oil film thickness of a floating bushing at each moment and determine a roller displacement and a floating bushing displacement at each moment during the rotation of a cam, a motion track determination module, configured to determine a roller motion track and a floating bushing motion track according to the roller displacement and the floating bushing displacement at each moment, respectively, a second parameter determination module, configured to determine, when the roller motion track and the floating bushing motion track are closed end to end, a minimum value of the inner-layer oil film thickness and a minimum value of the outer-layer oil film thickness of the floating bushing according to the inner-layer oil film thickness and the outer-layer oil film thickness of the floating bushing at each moment, respectively, and a double-layer oil film lubrication analysis module, configured to determine that an abnormality exists in double-layer oil film lubrication when either of the minimum value of the inner-layer oil film thickness and the minimum value of the outer-layer oil film thickness of the floating bushing is less than a preset oil film thickness threshold value.

In a third aspect, the present disclosure provides an electronic device including a memory, a processor, and a computer program stored in the memory and capable of running on the processor, which, when executing the program, implements a double-layer oil film lubrication analysis method based on a floating bushing.

In a fourth aspect, the present disclosure provides a non-transitory computer readable storage medium having a computer program stored thereon, which, when executed by a processor, implements a double-layer oil film lubrication analysis method based on a floating bushing.

In the present disclosure, an inner-layer oil film thickness and an outer-layer oil film thickness of a floating bushing at each moment are determined and a roller displacement and a floating bushing displacement at each moment are determined during the rotation of a cam; a roller motion track and a floating bushing motion track are determined according to the roller displacement and the floating bushing displacement at each moment, respectively; a minimum value of the inner-layer oil film thickness and a minimum value of the outer-layer oil film thickness of the floating bushing are determined, when the roller motion track and the floating bushing motion track are closed end to end, according to the inner-layer oil film thickness and the outer-layer oil film thickness of the floating bushing at each moment, respectively; and an abnormality existing in double-layer oil film lubrication is determined when either of the minimum value of the inner-layer oil film thickness and the minimum value of the outer-layer oil film thickness of the floating bushing is less than a preset oil film thickness threshold value. That is, in the present disclosure, the kinematic and dynamic relationship between the cam and the roller is utilized and the real-time abnormality analysis of the double-layer oil film lubrication state of the floating bushing is performed in combination with the transient (each moment) lubrication parameters (oil film thickness related parameters) between the roller, the floating bushing and the roller pin, thereby realizing more accurate abnormality analysis and determination of the double-layer oil film lubrication of the floating bushing.

BRIEF DESCRIPTION OF THE DRAWINGS

In order to explain the technical solutions of the present disclosure or the prior art more clearly, the drawings needed in the description of the embodiments or the related art will be briefly introduced below. Obviously, the drawings in the following description are some embodiments of the present disclosure, and other drawings can be obtained according to the provided drawings without creative work for ordinary people in the field.

FIG. 1 is a first flow chart of a double-layer oil film lubrication analysis method based on a floating bushing according to the present disclosure;

DETAILED DESCRIPTION

Figure 2:
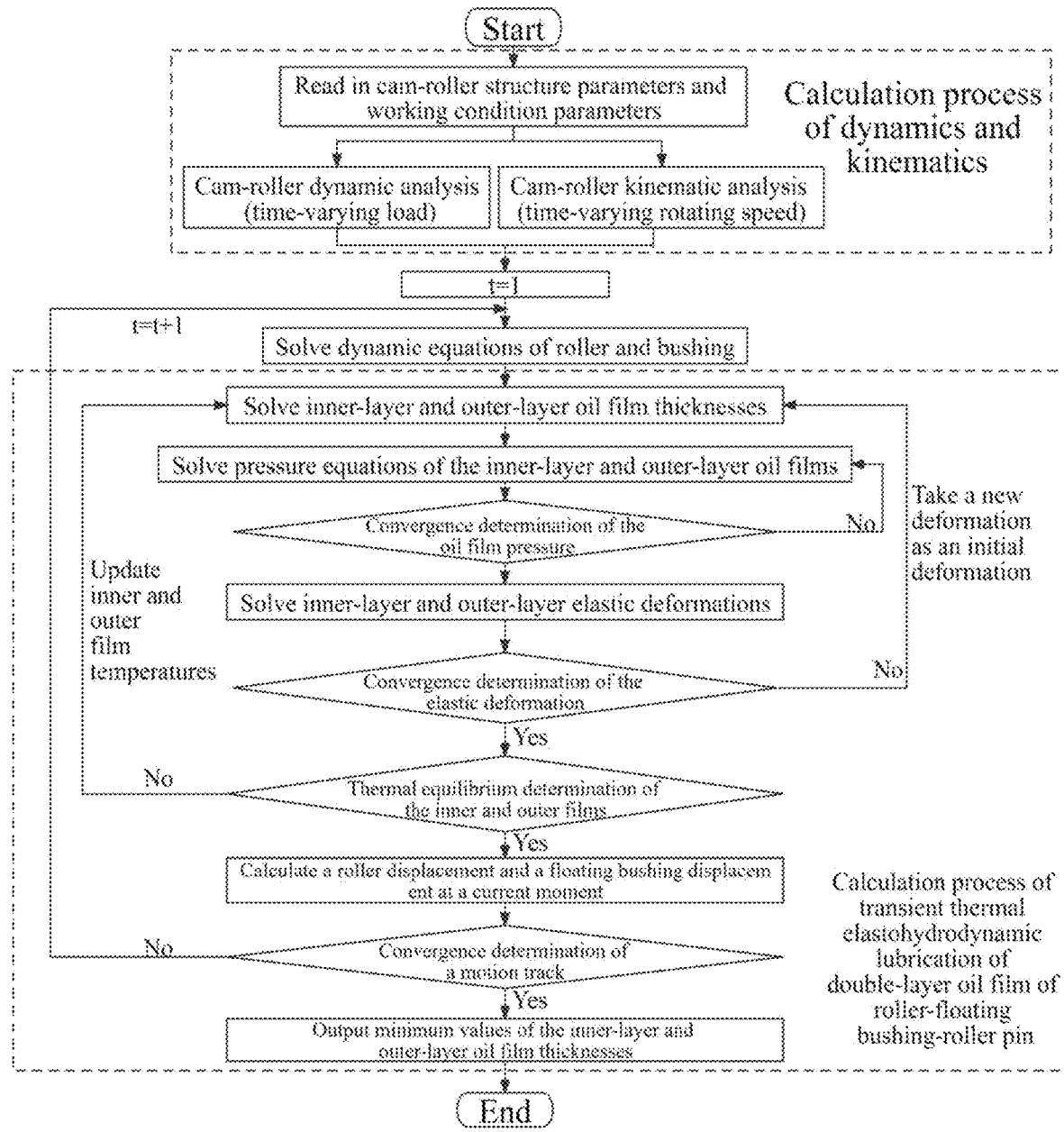
FIG. 2 is a second flow chart of the double-layer oil film lubrication analysis method based on a floating bushing according to the present disclosure.

In order to make the object, technical solutions and advantages of the present disclosure clearer, the technical solutions in the present disclosure are described clearly and completely below with reference to the attached drawings in the present disclosure. Obviously, all the described embodiments are only some, rather than all embodiments of the present disclosure. Based on the embodiments in the present disclosure, all other embodiments obtained by those of ordinary skill in the art without creative efforts belong to the scope of protection of the present disclosure.

A double-layer oil film lubrication analysis method based on a floating bushing of the present disclosure will be described below with reference to FIGS. 1 to 4. As shown in FIG. 1, a double-layer oil film lubrication analysis method based on a floating bushing includes the following steps.

At step 101: an inner-layer oil film thickness and an outer-layer oil film thickness of a floating bushing at each moment are determined and a roller displacement and a floating bushing displacement at each moment are determined during the rotation of a cam.

Fixed time steps are separated by various moments in each moment, and the time step is a preset value. According to the structural parameters of the first combination structure (including the cam and the roller) at each moment, the roller displacement and the floating bushing displacement at each moment are determined. The RANS equations of inner-layer and outer-layer oil films are solved by using the inner-layer oil film thickness and the outer-layer oil film thickness of the floating bushing at the current moment. When a pressure converges, an inner-layer oil film pressure and an outer-layer oil film pressure of the floating bushing at the current moment are obtained. An inner-layer elastic deformation and an outer-layer elastic deformation of the floating bushing are determined according to the inner-layer oil film pressure and the outer-layer oil film pressure, respectively. The inner-layer elastic deformation and the outer-layer elastic deformation are substituted into an oil film thickness equation. When the elastic deformations converge and the inner and outer layers of the floating bushing reach a thermal equilibrium condition, the inner-layer oil film thickness and the outer-layer oil film thickness of the floating bushing at the current moment are obtained; then the roller displacement and the floating bushing displacement at the current moment are calculated; a roller motion track and a floating bushing motion track at the current moment are determined according to the roller displacement and the floating bushing displacement at the moment; if either of the roller motion track and the floating bushing motion track is not closed end to end, then an inner-layer oil film thickness and an outer-layer oil film thickness of the floating bushing at a next moment are determined according to the structural parameters among the roller, the floating bushing and the roller pin at the next moment; and so on, thereby obtaining the inner-layer oil film thickness and the outer-layer oil film thickness of the floating bushing at each moment.

At step 102: a roller motion track and a floating bushing motion track are determined according to the roller displacement and the floating bushing displacement at each moment, respectively.

At step 103: a minimum value of the inner-layer oil film thickness and a minimum value of the outer-layer oil film thickness of the floating bushing are determined, when the roller motion track and the floating bushing motion track are closed end to end, according to the inner-layer oil film thickness and the outer-layer oil film thickness of the floating bushing at each moment, respectively.

At step 104: an abnormality existing in double-layer oil film lubrication is determined when either of the minimum value of the inner-layer oil film thickness and the minimum value of the outer-layer oil film thickness of the floating bushing is less than a preset oil film thickness threshold value.

Since the rotation of the cam will drive the roller to rotate, and the roller, the floating bushing and the roller pin constitute a linkage mechanism, in the present disclosure, an inner-layer oil film thickness and an outer-layer oil film thickness of a floating bushing at each moment can be determined and a roller displacement and a floating bushing displacement at each moment are determined during the rotation of a cam; a roller motion track and a floating bushing motion track are determined according to the roller displacement and the floating bushing displacement at each moment, respectively; a minimum value of the inner-layer oil film thickness and a minimum value of the outer-layer oil film thickness of the floating bushing are determined, when the roller motion track and the floating bushing motion track are closed end to end, according to the inner-layer oil film thickness and the outer-layer oil film thickness of the floating bushing at each moment, respectively; and an abnormality existing in double-layer oil film lubrication is determined when either of the minimum value of the inner-layer oil film thickness and the minimum value of the outer-layer oil film thickness of the floating bushing is less than a preset oil film thickness threshold value. That is, in the present disclosure, the kinematic and dynamic relationship between the cam and the roller is utilized and the real-time abnormality analysis of the double-layer oil film lubrication state of the floating bushing is performed in combination with the transient (each moment) lubrication parameters (pressure and temperature related parameters) between the roller, the floating bushing and the roller pin, thereby realizing more accurate abnormality analysis and determination of the double-layer oil film lubrication of the floating bushing.

In one specific embodiment, the detailed calculation processes of the above-mentioned steps 101-104 are as shown in FIG. 2, mainly including two parts: a calculation process of dynamics and kinematics between the cam and the roller, and an analysis process of double-layer oil film transient lubrication based on the roller, the floating bushing and the roller pin.

In one aspect, the calculation process of dynamics and kinematics includes two parts: the calculation of the time-varying load of the roller and the calculation of the time-varying rotating speed of the roller.

The time-varying load of the roller needs to be calculated based on combined action of forces.

Figure 3:
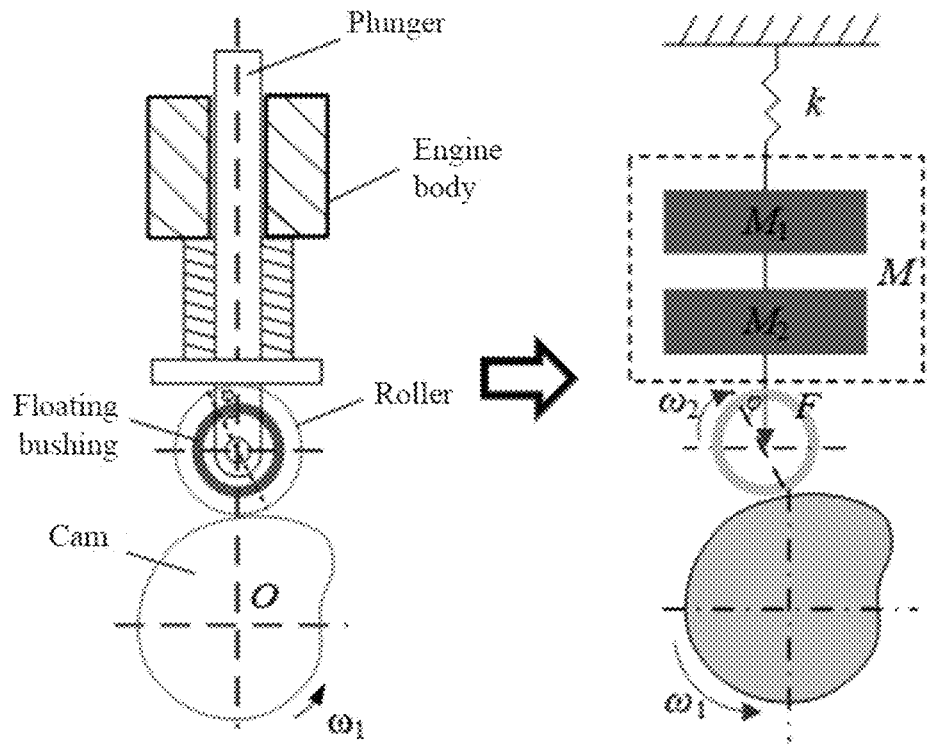
FIG. 3 is a schematic diagram of a dynamic model between a cam and a roller according to the present disclosure.

In one specific embodiment, a dynamic model between the cam and the roller is as shown in FIG. 3, and the specific calculation process of the time-varying load of the roller includes:

taking the mechanism as a rigid body, an expression of the time-varying load F on the roller being:

$$F=F_C+F_N+F_P$$

where, $F_C$ is an amount a restoring force of a spring converted to the roller, that is, an acting force of the spring on the roller;

$$F_C=F_0+c'\cdot s(\alpha)$$

where, $F_0$ is a spring pretightening force (N); $c'$ is a spring stiffness (N/m); $s(\alpha)$ is a roller lift (m); and $\alpha$ is a lift angle;

the inertial force $F_N$ being determined by the following equation:

$$F_N = M\omega_1^2 \frac{d^2s}{d\alpha^2}$$

where, $\omega_1$ is a rotating speed of the cam (rad/s); and M is a mass (kg) driven by the cam, a calculation formula being:

$$M = \frac{M_a}{3} + M_b + M_c + M_d$$

where, $M_a$ is a spring mass (kg); $M_b$ is a mass (kg) of other related parts in a cam mechanism except a plunger spring and the roller (such as a driven frame, etc.); $M_c$ is the plunger mass (kg); and $M_d$ is a roller mass (kg).

$F_P$ is a hydraulic pressure of a plunger oil chamber, a minimum value and a maximum value of the hydraulic pressure are known, and the change condition of the hydraulic pressure of the plunger oil chamber can be obtained by means of linear interpolation:

$$F_P = \frac{\pi \cdot d^2}{4} \cdot \left(P_1 + \frac{P_2 - P_1}{s_{max}} \cdot s\right)$$

where, d is a plunger diameter (m); $P_1$ is a minimum oil hydraulic pressure (MPa); $P_2$ is a maximum oil hydraulic pressure (MPa); and $s_{max}$ is a maximum roller lift.

For the calculation of the time-varying rotating speed of the roller, firstly, the structural parameters and operating conditions of the first combination structure (including the cam and the roller) are acquired; then a pressure angle and radius of curvature of the cam are calculated according to the cam profile parameters, and the cam surface speed is further calculated. Finally, the roller surface speed is calculated according to the speed relationship between the cam and the roller surfaces, and the roller time-varying rotating speed is calculated according to the roller surface speed.

Figure 4:
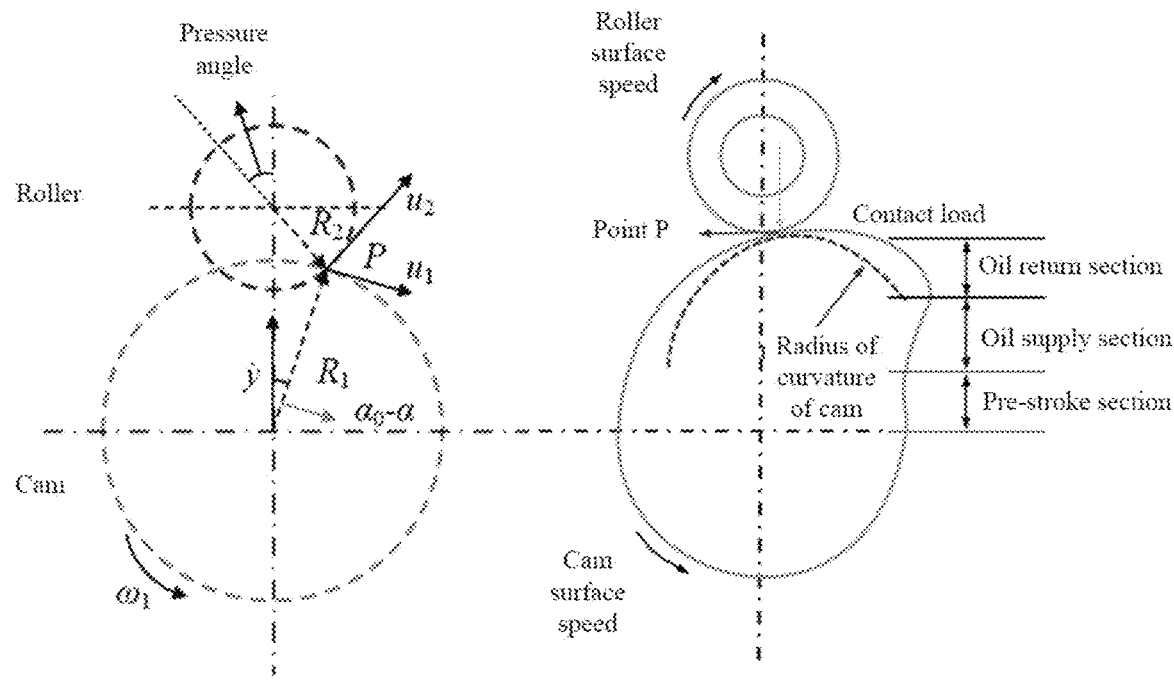
FIG. 4 is a schematic diagram of a dynamic model between a cam and a roller according to the present disclosure.

In one specific embodiment, a kinematic model between the cam and the roller is as shown in FIG. 4. FIG. 4 shows the kinematic parameters such as a radius of curvature and a pressure angle of the cam in the cam mechanism, and the specific calculation process of the time-varying rotating speed of the roller includes:

for the radius of curvature of the oil supply cam, the calculation formula being:

$$R_1 = \frac{\left[\left(\frac{dg}{d\alpha}\right)^2 + g^2(\alpha)\right]^{\frac{3}{2}}}{g^2(\alpha) + 2\left(\frac{dg}{d\alpha}\right)^2 - g(\alpha)\frac{d^2g}{d\alpha^2}} - R_2$$

where, $g(\alpha) = R_0 + R_2 + s(\alpha)$, a is a lift angle; $R_1$ is a radius of curvature of the cam (m): $R_0$ is a base radius (m) of the cam; and $R_2$ is an outer-ring radius of the roller (m).

For the combined radius of curvature of the cam and roller pair, the calculation formula is:

$$R = \frac{R_1 \cdot R_2}{R_1 + R_2}$$

A pressure angle $\varphi$ of the first combination structure (including the cam and the roller) changes with a rotating angle of the cam, being expressed as:

$$\varphi = \tan^{-1} \frac{\left|\frac{ds}{d\alpha} - e\right|}{s + \sqrt{R_0^2 - e^2}}$$

where, e is an eccentric distance (m); and s is a roller lift (m).

The speed relationship between the cam and the roller surfaces meets:

$$\begin{cases} u_1 = \omega_1 R \\ u_2 = u_1 \cos(\alpha_0 - \alpha)/\cos\varphi \end{cases}$$

where, $u_1$ and $u_2$ are linear velocities of a cam surface and a roller surface; $\omega_1$ is a time-varying rotating speed of the cam (rad/s), and $\alpha_0$ is a push angle. Therefore, a time-varying rotating speed $\omega_2$ of the roller can be expressed as:

$$\omega_2 = u_2/R_2$$

On the other hand, a double-layer oil film transient lubrication analysis process based on the roller, the floating bushing and the roller pin includes the following steps.

The thicknesses of the inner-layer and outer-layer oil films of the floating bushing at an initial moment (t=1) are calculated according to the structural parameters of the second combination structure (including the roller, the floating bushing, and the roller pin), an initial assumed position, an initial thermal deformation amount and an elastic deformation amount.

In one specific embodiment, the thickness equations for the inner-layer and outer-layer oil films of the floating bushing are:

$$h_i = (R_f - R_j + \delta_{Ti})(1 + \varepsilon_i \cos(\theta - \varphi_i)) + \delta_{Pi}$$

$$h_o = (R_b - R_o + \delta_{To})(1 + \varepsilon_o \cos(\theta - \varphi_o)) + \delta_{Po}$$

where, $h_i$ and $h_o$ are thicknesses of the inner-layer and outer-layer oil films of the floating bushing; $R_i$ and $R_o$ are inner-ring and outer-ring radiuses of the floating bushing; $R_b$ is an inner-ring radius of an outer roller; $\varepsilon_i$ and $\varepsilon_o$ are eccentricities of the inner and outer layers of the floating bushing; $\varphi_i$ and $\varphi_o$ are deviation angles of the inner and outer layers of the floating bushing; $R_j$ is a radius of the roller pin; $\delta_{Ti}$ and $\delta_{To}$ are gap variations caused by the thermal deformations of the inner and outer layers; and $\delta_{Pi}$ and $\delta_{Po}$ are the elastic deformation amounts of the inner and outer layers of the floating bushing.

On the basis of obtaining the thickness of the inner-layer and outer-layer oil films of the floating bushing, the RANS equations of the inner-layer and outer-layer oil films are solved by using the finite difference method based on the obtained time-varying rotating speed of the roller, and the pressures of the inner-layer and outer-layer oil films are obtained by loop iteration until the pressure convergence is satisfied; and in the loop iterative process, a pressure boundary condition adopts a Reynolds boundary condition.

In one specific embodiment, RANS equations for the inner-layer and outer-layer oil films are:

$$\frac{\partial}{R_i^2 \partial \theta}\left(\phi_x \frac{\rho h_i^3}{\mu_i} \frac{\partial p_i}{\partial \theta}\right) + \frac{\partial}{\partial y}\left(\phi_y \frac{\rho h_i^3}{\mu_i} \frac{\partial p_i}{\partial y}\right) =$$

$$6\omega_r \phi_c \frac{\partial(\rho h_i)}{\partial \theta} - 6\omega_r \sigma_i \frac{\partial(\rho \phi_s)}{\partial \theta} + 12\phi_c \frac{\partial h_i}{\partial t}$$

$$\frac{\partial}{R_o^2 \partial \theta}\left(\phi_x \frac{\rho h_o^3}{\mu_o} \frac{\partial p_o}{\partial \theta}\right) + \frac{\partial}{\partial y}\left(\phi_y \frac{\rho h_o^3}{\mu_o} \frac{\partial p_o}{\partial y}\right) =$$

$$6(\omega_r + \omega_2)\phi_c \frac{\partial(\rho h_o)}{\partial \theta} + 6(\omega_r - \omega_2)\sigma_o \frac{\partial(\rho \phi_s)}{\partial \theta} + 12\phi_c \frac{\partial h_o}{\partial t}$$

where, $\theta$ is a circumferential coordinate; y is an axial coordinate; $p_i$ and $p_o$ are pressures of the inner-layer and outer-layer oil films of the floating bushing; $\omega_r$ is a rotating speed of the floating bushing; $\omega_2$ is a rotating speed of the roller; $\phi_x$ and $\phi_y$ are pressure flow factors; $\phi_c$ is a contact factor; $\phi_s$ is a shear flow factor; $\sigma_i$ and $\sigma_o$ are surface comprehensive roughness of inner and outer layers; $\rho$ is a density of lubricating oil; and $\mu_i$ and $\mu_o$ are lubricating oil viscosities considering temperature viscosity effect in the inner and outer layers.

The elastic deformation amounts of various nodes of the inner and outer layers of the floating bushing are calculated correspondingly according to the pressures of the inner and outer layer oil films by using the deformation matrix method, the elastic deformation amounts of the inner and outer layers are substituted into the thickness equations of the inner and outer layer oil films of the floating bushing to determine the convergence of elastic deformation. If the convergence condition is satisfied, the loop is skipped, and if the convergence condition is not satisfied, the elastic deformation amount is updated, and the previous oil film pressure calculation is repeated.

In one specific embodiment, the elastic deformations of various nodes in the inner and outer layers of the floating bushing are calculated by using the deformation matrix method as:

$$\delta_{pi}(\theta, y) = \int_0^{L_i} \int_0^{2\pi} KI_{\theta,y}^{\theta',y'} p_i(\theta', y') d\theta dy$$

$$\delta_{po}(\theta, y) = \int_0^{L_o} \int_0^{2\pi} KO_{\theta,y}^{\theta',y'} p_o(\theta', y') d\theta dy$$

where, $\delta_{pi}(\theta, y)$ and $\delta_{po}(\theta, y)$ are elastic deformation amounts of the inner and outer layers of the floating bushing at a node $(\theta, y)$; $p_i(\theta, y)$ and $p_o(\theta, y)$ are oil film pressures of the inner and outer layers of the floating bushing at the node $(\theta, y)$; and $KI_{\theta,y}^{\theta',y'}$ and $KO_{\theta,y}^{\theta',y'}$ are elastic deformation matrixes of the inner and outer layers of the floating bushing, that is, the elastic deformation generates at the $(\theta, y)$ node when unit pressure acts at a surface node $(\theta', y')$.

A balance temperature of the inner-layer and outer-layer oil films is calculated by using thermal equilibrium equations of the inner-layer and outer-layer oil films. That is, whether the friction thermal generation and the end heat release satisfy the same condition is determined, and if not, temperatures of the inner-layer and outer-layer oil films are updated and then inner-layer and outer-layer thermal deformation amounts are calculated according to the updated temperatures of the inner-layer and outer-layer oil films, and an initial thermal deformation amount is updated; if so, based on the time-varying load of the roller, the kinematic equations of the roller and the floating bushing and the rotating speed equation of the floating bushing are solved by the difference method, and the roller displacement, the floating bushing displacement and the rotating speed of the floating bush at a next moment are obtained.

When loop iterations are performed at various moments, after a calculation result of the current moment satisfies a determination condition, a fixed time step is added to the current moment to obtain a next moment; and the time step of the interval between various moments is fixed, and the time step is a preset value. For example, when t=1, if the thermal equilibrium condition of the inner and outer films is satisfied, a fixed time step is added to t=1 to obtain t=2; when t=2, if the thermal equilibrium condition of the inner and outer films is satisfied, a fixed time step is added to t=2 to obtain t=3, and so on.

In one specific embodiment, the thermal equilibrium equations of the inner-layer and outer-layer oil films are:

$$c_p \rho Q_i \Delta T_i = W_i$$

$$c_p \rho Q_o \Delta T_o = W_o$$

where, $c_p$ is a specific heat of the lubricating oil; $\rho$ is a density of the lubricating oil; $\Delta T_i$ and $\Delta T_o$ are the inner-layer and outer-layer temperature rises; and $Q_i$ and $Q_o$ are the inner-layer and outer-layer end discharge volumes, the calculation formulas being:

$$Q_i = 2 \int_0^{2\pi R_i} \left[-\frac{h_i^3}{12\mu_i} \frac{\partial p_i}{\partial y}\right]_{y=L_i} dx$$

$$Q_o = 2 \int_0^{2\pi R_o} \left[-\frac{h_o^3}{12\mu_o} \frac{\partial p_o}{\partial y}\right]_{y=L_o} dx$$

where, $y=L_i$ and $y=L_o$ refer to end side positions of the inner and outer layers of the floating bushing;

$W_i$ and $W_o$ are friction losses of the inner and outer layers, the calculation formulas being:

$$W_i = \int_0^{L_i} \int_0^{2\pi R_i} \left\{\frac{h_i^3}{2}\left[\left(\frac{\partial p_i}{\partial x}\right)^2 + \left(\frac{\partial p_i}{\partial y}\right)^2\right] + \frac{\mu_i}{h_i}\omega_r^2 R_i^2\right\} dxdy$$

$$W_o = \int_0^{L_o} \int_0^{2\pi R_o} \left\{\frac{h_o^3}{2}\left[\left(\frac{\partial p_o}{\partial x}\right)^2 + \left(\frac{\partial p_o}{\partial y}\right)^2\right] + \frac{\mu_o}{h_o}(\omega_2 - \omega_r)^2 R_0^2\right\} dxdy$$

In one specific embodiment, the calculation formulas of the thermal deformation amounts of the inner and the outer layers are:

$$\delta_{Ti} = \alpha_R R_i \Delta T_i - \alpha_J R_j \Delta T_i$$

$$\delta_{To} = \alpha_B R_b \Delta T_o - \alpha_R R_o \Delta T_o$$

where, $\delta_{Ti}$ is a thermal deformation amount of the inner layer, $\delta_{To}$ is a thermal deformation amount of the outer layer, and $\alpha_J$, $\alpha_R$ and $\alpha_B$ are thermal expansion coefficients of the roller pin, the floating bushing and the roller.

In one specific embodiment, a kinematic equation of the roller is:

$$\begin{cases} m_1 \ddot{y}_1 = F + P_{yo} \\ m_1 \ddot{x}_1 = P_{xo} \end{cases}$$

The kinematic equation of the floating bushing is:

$$\begin{cases} m_2 \ddot{y}_2 = P_{yi} - P_{yo} \\ m_2 \ddot{x}_2 = P_{xi} - P_{xo} \end{cases}$$

The speed rotating equation of the floating bushing is:

$$I_2 \dot{\omega}_r = \Gamma_i - \Gamma_o$$

where, $m_1$ is a roller mass, $m_2$ is a floating bushing mass, F is a time-varying load on the roller, $P_{xi}$ and $P_{yi}$ are oil film bearing capacities of the inner layer of the floating bushing in the horizontal and vertical directions, $P_{xo}$ and $P_{yo}$ are oil film bearing capacities of the outer layer of the floating bushing in the horizontal and vertical directions, $\Gamma_i$ and $\Gamma_o$ correspond to friction torques of the inner and outer layer oil films, and $I_2$ is a rotational inertia of the floating bushing, $\dot{\omega}_r$ is an angular accelerated speed of the floating bushing, $\ddot{x}_1$ and $\ddot{y}_1$ correspond to the horizontal and vertical accelerated speeds of the roller, and $\ddot{x}_2$ and $\ddot{y}_2$ corresponds to the horizontal and vertical accelerated speeds of the floating bushing.

The roller motion track and the floating bushing motion track can be obtained according to the roller displacement and the floating bushing displacement and the rotating speed of the floating bushing at various moments; when the roller motion track and the floating bushing motion track are closed end to end, that is, when the tracks are stable, a loop is skipped at this moment, and the minimum value of the inner-layer oil film thickness and the minimum value of the outer-layer oil film thickness of the floating bushing are output; an abnormality existing in double-layer oil film lubrication is determined when either of the minimum value of the inner-layer oil film thickness and the minimum value of the outer-layer oil film thickness is less than a preset oil film thickness threshold value; and when either of the roller motion track and the floating bushing motion track is not closed end to end, an initial displacement of the roller, an initial displacement of the floating bushing, and an initial rotating speed of the floating bushing are updated and the iteration continues.

In one specific embodiment, the present disclosure can also determine whether it is necessary to skip the loop by determining whether the correspondingly obtained roller motion track and floating bushing motion track are stable when the cam angle rotates by 360°; when both tracks are closed end to end (namely, stable), the loop is skipped; and the minimum value of the inner-layer oil film thickness and the minimum value of the outer-layer oil film thickness of the floating bushing are output; an abnormality existing in double-layer oil film lubrication is determined when either of the minimum value of the inner-layer oil film thickness and the outer-layer oil film thickness of the floating bushing is less than a preset oil film thickness threshold value; and when either of the roller motion track and the floating bushing motion track is not closed end to end, the initial displacement of the roller, the initial displacement of the floating bushing, and the initial rotating speed of the floating bushing are updated and the iteration continues.

In one specific embodiment, the preset oil film thickness threshold value is any value in a range of 0.8 microns to 1.2 microns.

According to the embodiments provided by the present disclosure, the present disclosure also discloses the following technical effects.

1. According to the present disclosure, the thermo-elastic deformations of the inner and outer layers of the floating bushing, and the mixed lubrication effect of the inner-layer and outer-layer oil films of the floating bushing are considered, which is more in line with the actual lubrication state, so that the double-layer oil film lubrication state determination based thereon is more accurate.

2. According to the present disclosure, the kinematic and dynamic relationship between the cam and the roller is coupled with the transient mixed thermal elastohydro-dynamic lubrication of the double-layer oil film among the roller, the floating bushing and the roller pin, and the time-varying rotating speed and time-varying load of the roller are considered to more accurately reflect the working conditions of the roller, the floating bushing and the roller pin at various moments, and based on this, the accuracy of the analysis of the double-layer oil film lubrication state of the floating bushing can be improved.

The double-layer oil film lubrication analysis system based on a floating bushing provided by the present disclosure is described below, and the following description of the double-layer oil film lubrication analysis system based on a floating bushing and the above description of the double-layer oil film lubrication analysis method based on a floating bushing may refer to each other correspondingly.

Figure 5:
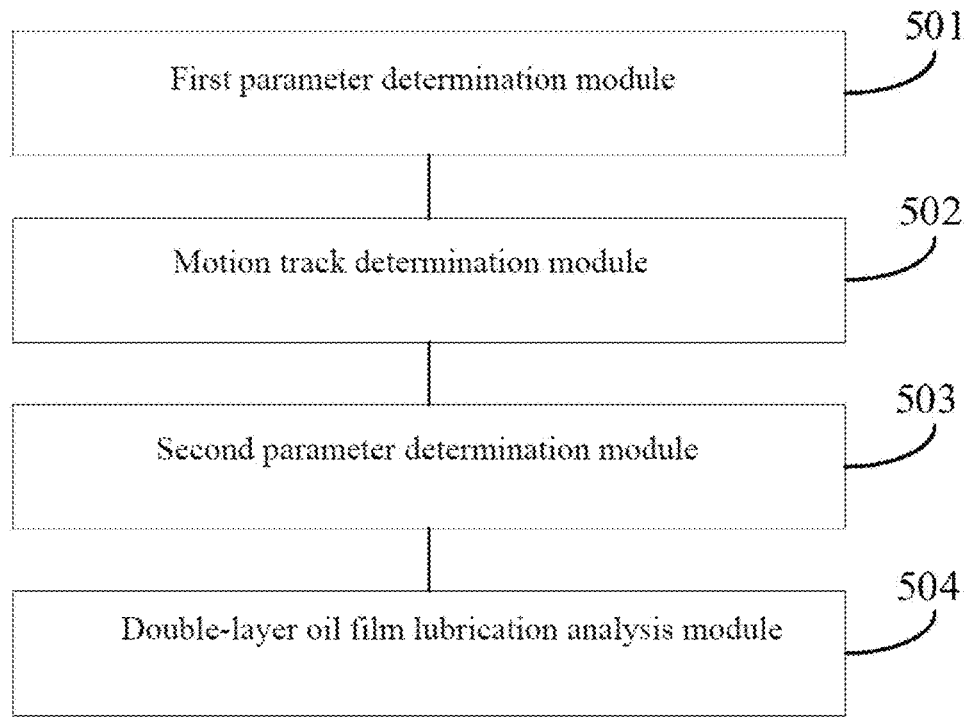
FIG. 5 is a module diagram of a double-layer oil film lubrication analysis system based on a floating bushing according to the present disclosure.

As shown in FIG. 5, a double-layer oil film lubrication analysis system based on a floating bushing includes:

a first parameter determination module 501, configured to determine an inner-layer oil film thickness and an outer-layer oil film thickness of a floating bushing at each moment and determine a roller displacement and a floating bushing displacement at each moment during the rotation of a cam;

a motion track determination module 502, configured to determine a roller motion track and a floating bushing motion track according to the roller displacement and the floating bushing displacement at each moment, respectively;

a second parameter determination module 503, configured to determine, when the roller motion track and the floating bushing motion track are closed end to end, a minimum value of the inner-layer oil film thickness and a minimum value of the outer-layer oil film thickness of the floating bushing according to the inner-layer oil film thickness and the outer-layer oil film thickness of the floating bushing at each moment, respectively; and a double-layer oil film lubrication analysis module 504, configured to determine that an abnormality exists in double-layer oil film lubrication when either of the minimum value of the inner-layer oil film thickness and the minimum value of the outer-layer oil film thickness of the floating bushing is less than a preset oil film thickness threshold value.

Figure 6:
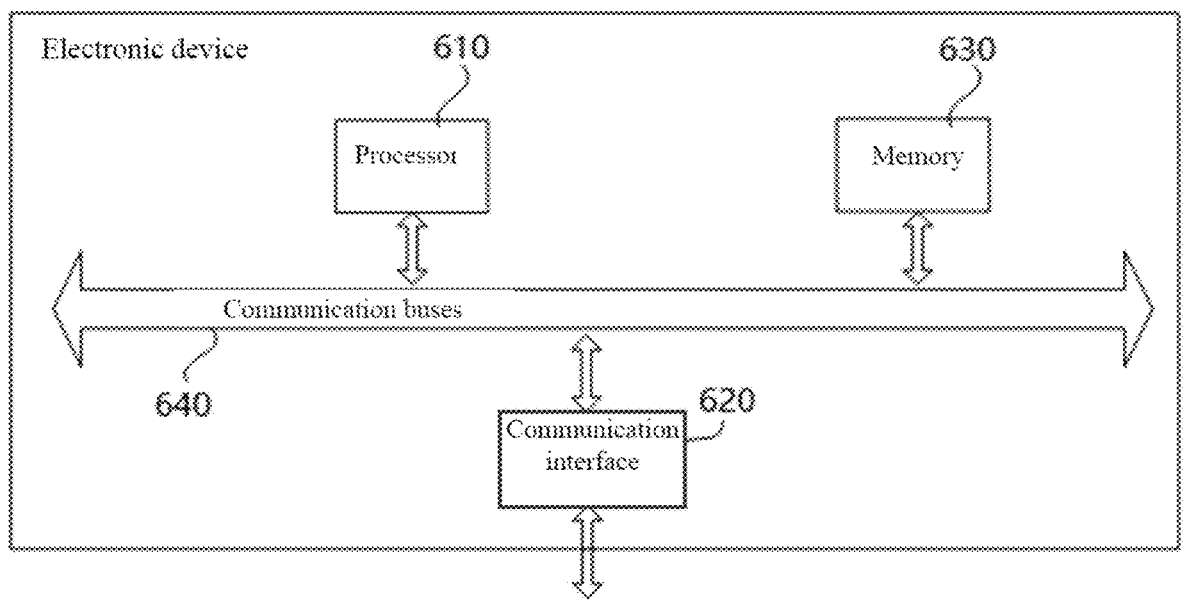
FIG. 6 is a schematic structural diagram of an electronic device provided by the present disclosure.

FIG. 6 illustrates a physical structure diagram of an electronic device, and as shown in FIG. 6, the electronic device can include: a processor 610, a communication interface 620, a memory 830 and communication buses 640, the processor 610, the communication interface 620 and the memory 630 communicating with each other via the communication buses 640. The processor 610 may call logic instructions in the memory 630 to perform a double-layer oil film lubrication analysis method based on a floating bushing, including the following steps.

An inner-layer oil film thickness and an outer-layer oil film thickness of a floating bushing at each moment are determined and a roller displacement and a floating bushing displacement at each moment are determined during the rotation of a cam.

A roller motion track and a floating bushing motion track are determined according to the roller displacement and the floating bushing displacement at each moment, respectively.

A minimum value of the inner-layer oil film thickness and a minimum value of the outer-layer oil film thickness of the floating bushing are determined, when the roller motion track and the floating bushing motion track are closed end to end, according to the inner-layer oil film thickness and the outer-layer oil film thickness of the floating bushing at each moment, respectively.

An abnormality existing in double-layer oil film lubrication is determined when either of the minimum value of the inner-layer oil film thickness and the minimum value of the outer-layer oil film thickness of the floating bushing is less than a preset oil film thickness threshold value.

Furthermore, the logic instructions in the memory 630 described above may be implemented in the form of software functional units and may be stored in a computer-readable storage medium when sold or used as an independent product. Based on such an understanding, the technical solution of the present disclosure, in essence or in part contributing to the prior art or in part of the technical solution, may be embodied in the form of a software product stored on a storage medium including several instructions for causing a computer device (which may be a personal computer, a server, or a network device, etc.) to perform all or part of the steps of the method according to various embodiments of the present disclosure. The storage medium described above includes: various media that can store the program codes, such as a U-disk, a mobile hard disk, a read-only memory (ROM), a random access memory (RAM), a magnetic disk or an optical disk.

In another aspect, the present disclosure also provides a computer program product including a computer program storable on a non-transitory computer-readable storage medium, the computer program, when executed by a processor, being executed by a computer to perform a double-layer oil film lubrication analysis method based on a floating bushing, the method including the following steps.

An inner-layer oil film thickness and an outer-layer oil film thickness of a floating bushing at each moment are determined and a roller displacement and a floating bushing displacement at each moment are determined during the rotation of a cam.

A roller motion track and a floating bushing motion track are determined according to the roller displacement and the floating bushing displacement at each moment, respectively.

A minimum value of the inner-layer oil film thickness and a minimum value of the outer-layer oil film thickness of the floating bushing are determined, when the roller motion track and the floating bushing motion track are closed end to end, according to the inner-layer oil film thickness and the outer-layer oil film thickness of the floating bushing at each moment, respectively.

An abnormality existing in double-layer oil film lubrication is determined when either of the minimum value of the inner-layer oil film thickness and the minimum value of the outer-layer oil film thickness of the floating bushing is less than a preset oil film thickness threshold value.

In yet another aspect, the present disclosure also provides a non-transitory computer-readable storage medium having a computer program stored thereon, which, when executed by a processor, implements to perform a double-layer oil film lubrication analysis method based on a floating bushing, the method including the following steps.

An inner-layer oil film thickness and an outer-layer oil film thickness of a floating bushing at each moment are determined and a roller displacement and a floating bushing displacement at each moment are determined during the rotation of a cam.

A roller motion track and a floating bushing motion track are determined according to the roller displacement and the floating bushing displacement at each moment, respectively.

A minimum value of the inner-layer oil film thickness and a minimum value of the outer-layer oil film thickness of the floating bushing are determined, when the roller motion track and the floating bushing motion track are closed end to end, according to the inner-layer oil film thickness and the outer-layer oil film thickness of the floating bushing at each moment, respectively.

An abnormality exists in double-layer oil film lubrication is determined when either of the minimum value of the inner-layer oil film thickness and the minimum value of the outer-layer oil film thickness of the floating bushing is less than a preset oil film thickness threshold value.

The embodiments of the apparatus described above are merely schematic, the units illustrated as separate elements may or may not be physically separated, and the elements shown as units may or may not be physical units, that is, the units and elements may be located in one place, or may also be distributed on a plurality of network units. Some or all of the modules may be selected to achieve the objectives of the embodiment solutions according to actual needs. Those of ordinary skill in the art can understand and implement the solutions without creative efforts.

From the description of the above implementations, as can be clearly understood by those skilled in the art, various implementations can be implemented by means of software and a necessary general hardware platform, but of course also by means of hardware. Based on such an understanding, the technical solution described above, in essence or in part contributing to the prior art, may be embodied in the form of a software product, which may be stored on a computer-readable storage medium (such as a ROM/RAM, magnetic disk, optical disk, etc.), including several instructions for causing a computer device (which may be a personal computer, a server, or a network device, etc.) to perform the methods of the various embodiments or some parts of the embodiments.

Finally, it is to be noted that the above embodiments are only used to illustrate the technical solutions of the present disclosure, but not to limit this. Although the present disclosure has been described in detail with reference to the foregoing embodiments, the technical solutions described in the foregoing embodiments can still be modified, or some technical features can be replaced by equivalents; while these modifications or substitutions do not make the essence of the corresponding technical solutions deviate from the spirit and scope of the technical solutions of various embodiments of the present disclosure.

What is claimed is:

1. A double-layer oil film lubrication analysis method based on a floating bushing, comprising:
   determining an inner-layer oil film thickness and an outer-layer oil film thickness of a floating bushing at each of a plurality of moments and determining a roller displacement and a floating bushing displacement at each of the plurality of moments during rotation of a cam, determining a roller motion track and a floating bushing motion track according to the roller displacement and the floating bushing displacement at each of the plurality of moments, respectively, determining, when the roller motion track and the floating bushing motion track are closed end to end, a minimum value of the inner-layer oil film thickness and a minimum value of the outer-layer oil film thickness of the floating bushing according to the inner-layer oil film thickness and the outer-layer oil film thickness of the floating bushing at each of the plurality of moments, respectively, and determining that an abnormality exists in double-layer oil film lubrication when either of the minimum value of the inner-layer oil film thickness and the minimum value of the outer-layer oil film thickness of the floating bushing is less than a preset oil film thickness threshold value, wherein the determining an inner-layer oil film thickness and an outer-layer oil film thickness of a floating bushing at each of a plurality of moments moment comprises:

calculating an inner-layer oil film thickness and an outer-layer oil film thickness of the floating bushing at a current moment according to structural parameters of a second combination structure, the second combination structure comprising a roller, a floating bushing and a roller pin;

determining a roller motion track and a floating bushing motion track at the current moment according to the roller displacement and the floating bushing displacement, and acquiring structural parameters of the second combination structure at a next moment if either of the roller motion track and the floating bushing motion track is not closed end to end; and determining an inner-layer oil film thickness and an outer-layer oil film thickness of the floating bushing at the next moment according to the structural parameters of the second combination structure at the next moment.

2. The double-layer oil film lubrication analysis method based on a floating bushing according to claim 1, wherein the determining an inner-layer oil film thickness and an outer-layer oil film thickness of a floating bushing at each of a plurality of moments specifically comprises:

acquiring structural parameters of a first combination structure, the first combination structure comprising a cam and a roller;

calculating a time-varying rotating speed of the roller according to the structural parameters of the first combination structure;

acquiring the structural parameters of the second combination structure, the second combination structure comprising the roller, the floating bushing and the roller pin;

calculating the inner-layer oil film thickness and the outer-layer oil film thickness of the floating bushing at the current moment according to the structural parameters of the second combination structure;

solving Reynolds-averaged Navier-Stokes (RANS) equations of the inner-layer and outer-layer oil films according to the time-varying rotating speed of the roller, the inner-layer oil film thickness and the outer-layer oil film thickness, and obtaining an inner-layer oil film pressure and an outer-layer oil film pressure of the floating bushing at the current moment when a pressure converges;

determining an inner-layer elastic deformation and an outer-layer elastic deformation of the floating bushing according to the inner-layer oil film pressure and the outer-layer oil film pressure, respectively;

substituting the inner-layer elastic deformation and the outer-layer elastic deformation into an oil film thickness equation, and outputting the inner-layer oil film pressure and the outer-layer oil film pressure of the floating bushing at the current moment when the elastic deformations converge and the inner and outer layers of the floating bushing reach a thermal equilibrium condition;

determining a roller displacement and a floating bushing displacement at the current moment;

determining the roller motion track and the floating bushing motion track at the current moment according to the roller displacement and the floating bushing displacement;

acquiring the structural parameters of the second combination structure at the next moment if either of the roller motion track and the floating bushing motion track is not closed end to end; and determining the inner-layer oil film thickness and the outer-layer oil film thickness of the floating bushing at the next moment according to the structural parameters of the second combination structure at the next moment.

3. The double-layer oil film lubrication analysis method based on a floating bushing according to claim 2, wherein the calculating a time-varying rotating speed of the roller according to the structural parameters of the first combination structure specifically comprises:

calculating a pressure angle and radius of curvature of the cam according to cam profile parameters;

calculating a cam surface speed according to the pressure angle and radius of curvature of the cam;

calculating a roller surface speed according to the cam surface speed; and calculating the time-varying rotating speed of the roller according to the roller surface speed.

4. The double-layer oil film lubrication analysis method based on a floating bushing according to claim 1, wherein the determining a roller displacement and a floating bushing displacement at each of the plurality of moments specifically comprises:

acquiring structural parameters of a first combination structure, the first combination structure comprising a cam and a roller;

calculating a time-varying load of the roller according to the structural parameters of the first combination structure; and determining a roller displacement and a floating bushing displacement at each of the plurality of moments according to the time-varying load of the roller and a kinematic equation between the roller and the floating bushing.

5. The double-layer oil film lubrication analysis method based on a floating bushing according to claim 4, wherein the time-varying load of the roller comprises a spring-to-roller acting force, an inertial force, and a plunger oil chamber hydraulic pressure.

6. The double-layer oil film lubrication analysis method based on a floating bushing according to claim 1, wherein the preset oil film thickness threshold value is any value in a range of 0.8 microns to 1.2 microns.

7. An electronic device comprising a memory, a processor, and a computer program stored in the memory and capable of running on the processor, which, when executing the program, implements the double-layer oil film lubrication analysis method based on a floating bushing according to claim 1.

8. The electronic device according to claim 7, wherein the computer program, when executed by the processor, implements a double-layer oil film lubrication analysis method based on a floating bushing according to claim 2.

9. The electronic device according to claim 7, wherein the computer program, when executed by the processor, implements a double-layer oil film lubrication analysis method based on a floating bushing according to claim 3.

10. The electronic device according to claim 7, wherein the computer program, when executed by the processor, implements a double-layer oil film lubrication analysis method based on a floating bushing according to claim 4.

11. The electronic device according to claim 7, wherein the computer program, when executed by the processor, implements a double-layer oil film lubrication analysis method based on a floating bushing according to claim 5.

12. The electronic device according to claim 7, wherein the computer program, when executed by the processor, implements a double-layer oil film lubrication analysis method based on a floating bushing according to claim 6.

* * * * *